United States Patent [19]

Metzger

[11] Patent Number: 4,529,591
[45] Date of Patent: Jul. 16, 1985

[54] SYNERGISTIC MIXTURES OF PENICILLINS

[75] Inventor: Karl G. Metzger, Wuppertal, Fed. Rep. of Germany

[73] Assignee: Bayer Aktiengesellschaft, Leverkusen, Fed. Rep. of Germany

[21] Appl. No.: 353,656

[22] Filed: Mar. 1, 1982

Related U.S. Application Data

[63] Continuation of Ser. No. 932,057, Aug. 8, 1978, abandoned.

[30] Foreign Application Priority Data

Aug. 20, 1977 [DE] Fed. Rep. of Germany ....... 2737673

[51] Int. Cl.³ .................... A61K 35/00; A61K 35/74
[52] U.S. Cl. .................................................. 424/114
[58] Field of Search ........................................ 424/114

[56] References Cited

U.S. PATENT DOCUMENTS 3,949,077  4/1976  Buzwa et al. .................... 424/114

OTHER PUBLICATIONS

Chemical Abstracts, 67: 80901r, (1967).
Chemical Abstracts, 71: 36594b, (1969).
Chemical Abstracts, 82: 31313b, (1975).

Primary Examiner—Jerome D. Goldberg
Attorney, Agent, or Firm—Sprung, Horn, Kramer & Woods

[57] ABSTRACT

Synergistic anti-bacterial compositions comprising (A) D-α-[(imidazolidin-2-on-1-yl)-carbonylamino]-benzylpenicillin or D-α-[(3-methylsulphonyl-imidazolidin-2-on-1-yl)-carbonylamino]-benzylpenicillin, and (B) 3-(2,6-dichlorophenyl)-5-methyl-4-isoxazolylpenicillin, 3-(2-chloro-6-fluorophenyl)-5-methyl-4-isoxazolylpenicillin, 3-(2-chlorophenyl)-5-methyl-4-isoxazolylpenicillin, 3-phenyl-5-methyl-4-isoxazolylpenicillin, or 2,6-dimethoxyphenylpenicillin, or salts thereof. They can be used to fight infection, as additives to animal feeds to promote growth, and as a preservative for polymers.

7 Claims, No Drawings

SYNERGISTIC MIXTURES OF PENICILLINS

This is a continuation of application Ser. No. 932,057, filed Aug. 8, 1978, now abandoned.

The invention relates to new antibiotic synergistic combinations of certain known penicillins. The synergistic active compound combinations of the present invention comprise at least one compound from each of two groups of active compounds. The active compounds of the first group (group A) are the known penicillins D-α-[(imidazolidin-2-on-1-yl)-carbonylamino]-benzylpenicillin (U.S. Pat. No. 3,933,795) and D-α-[(3-methylsulphonyl-imidazolidin-2-on-1-yl)carbonylamino]-benzylpenicillin (German Offenlegungschrift (German Published Specification) No. 2,152,967). The active compounds of the selected group (group B) are the known penicillins 3-(2,6-dichlorophenyl-5-methyl-4-isoxazolylpenicillin, 3-(2-chloro-6-fluorophenyl)-5-methyl-4-isoxazolylpenicillin, 3-(2-chlorophenyl)-5-methyl-4-isoxazolylpenicillin, 3-phenyl-5-methyl-4-isoxazolylpenicillin and 2,6-dimethoxyphenylpenicillin.

Thus the present invention provides a pharmaceutical composition containing as active ingredients (A) a compound which is D-α-[(imidazolidin-2-on-1-yl)-carbonylamino]benzylpenicillin and/or D-α-[(3-methylsulphonyl-imidazolidin-2-on-1-yl)-carbonylamino]-benzylpenicillin and/or a salt thereof, and (B) a compound which is 3-(2,6-dichlorophenyl)-5-methyl-4-isoxazolylpenicillin, 3-(2-chloro-6-fluorophenyl)-5-methyl-4-isoxazolylpenicillin, 3-(2-chlorophenyl)5-methyl-4-isoxazolylpenicillin, 3-phenyl-5-methyl-4-isoxazolylpenicillin, and/or 2,6-dimethoxyphenylpenicillin and/or a salt thereof.

It is known that broad spectrum penicillins, such as α-carboxy-benzylpenicillin, α-amino-benzylpenicillin or α-carboxy-3-thienylmethylpenicillin, have no action or little action against certain species of bacteria because these bacteria from enzymes which split the β-lactam ring. It is also known that adding penicillins from active compound group B, which are stable towards the action of β-lactamases, can lead to synergism. This is recognized by the fact that the resistance of the β-lactamase-forming bacteria towards, for example, α-carboxybenzylpenicillin or α-aminobenzylpenicillin is removed or greatly descreased by adding penicillins from the active compound group B (see, for example, German Offenlegungsschrift No. 2,062,938). However, such synergistic effects have not hitherto been observed, for example, in the case of bacteria the genus of β-lactamase-forming Klebsiellae because ampicillin has no action or very little action against Klebsiellae.

Surprisingly, it has now been found, for the first time, that the new active compound combinations according to the invention have a powerful synergistic effect against these genera of bacteria. This is all the more surprising since the penicillins of active compound group A according to the invention cause very mush less lysis of bacteria than for example α-aminobenzylpenicillin.

The molar ratio of the active comounds from group A to those from group B can be in the range of about 9:1 to 1:9. It is preferably in the range of about 9:1 3, and is most preferably about 1:1.

Of the active compounds from group A, the penicillin D-α-[(3-methylsulphonyl-imidazolidin-2-on-1-yl)-carbonylamino]-benzylpenicillin is preferred. Of the active compounds from group B, the penicillin 3-phenyl-5-methyl-4-isoxazolylpenicillin is preferred.

The active compounds in the combination, according to the invention, of active compounds from group A with those from group B can be in the acid form or salt form as well as in any of the possible crystal forms and hydrate forms. Among the salts of the compounds from groups A and B, those salts that are pharmaceutically acceptable are particularly important and are preferred.

The pharmaceutically acceptable salts are in particular salts of the acid carboxyl group of the active compounds with inorganic or organic bases which have pharmaceutically acceptable cations.

Bases which can be employed for this are all the bases customarily used in pharmaceutical chemistry, in particular in the chemistry of antibiotics. Examples of inorganic bases which may be mentioned are: alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate and sodium bicarbonate and potassium bicarbonate; and aluminum hydroxide and ammonium hydroxide. Organic amines which can be employed are primary, secondary and tertiary aliphatic amines as well as heterocyclic amines. Examples which may be mentioned are: di-lower alkylamines and tri-lower alkylamines, for example diethylamine, triethylamine, tri-β-hydroxyethylamine, procaine, dibenzylamine, N,N'-dibenzylethylenediamine, N-benzyl-β-phenyl-ethylamine, N-methyl- and N-ethyl-morpholine, 1-ephenamine, dehydroabietylamine, N,N'-bis-dehydroabietylethylenediamine and N-lower alkylpiperidines.

So-called basic aminoacids, such as lysine or arginine, can als be advantageously used as bases. Particularly preferred salts are the sodium salts.

The synergistic active compound mixtures according to the invention display a powerful and broad antimicrobial activity, coupled with low toxicity. These properties enable them to be used as chemotherapeutic active compounds in medicine and as substances for preserving inorganic and organic materials, especially organic materials of all kinds, for example polymers, lubricants, paints, fibers, leather, paper and timber, and foodstuffs and water.

The synergistic active compound mixtures according to the invention are active against a very broad spectrum of micro-organisms. With their aid it is possible, for the first time, to combat Gram-negative and Gram-positive bacteria and bacteria-like micro-organisms without problems, and to prevent, alleviate and/or cure diseases caused by these pathogens.

The synergistic active compound mixtures according to the invention are particularly active against bacteria and bacteria-like micro-organisms. They are therefore particularly suitable for use in prophylaxis and chemotherapy, in human medicine and veterinary medicine, of local and systemic infections caused by these pathogens.

For example, local and/or systemic diseases which are caused by the following pathogens or by a mixture of the following pathogens can be treated and/or prevented:

Enterobacteriaceae, such as Escherichiae bacteria of the Coli group: Escherichia bacteria, for example *Escherichia coli*, Klebsiella bacteria, for example *K. pneumo-*

*niae,* and Proteae bacteria of the Proteus group: Proteus, for example *Proteus vulgaris, Pr. morganii* and *Pr. rettgeri.*

The above list of pathogens is purely illustrative and is in no way to be interpreted as restrictive.

Examples which may be mentioned of diseases which can be prevented, alleviated and/or cured by the synergistic active compound mixtures according to the invention are: diseases of the respiratory passages and of the pharyngeal cavity; otitis; pharyngitis; pneumonia; peritonitis; pyelonephritis; cystitis; endocarditis; systemic infections; bronchitis; arthritis; and local infections.

As stated above, the invention also relates to the use in human and veterinary medicine of the compounds of the invention.

The present invention provides a pharamaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredients can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5, usually from 0.5 to 95% of the acitve ingredient by weight of the total composition.

In addition to compounds of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is from 250 mg to 50 g, preferably from 1 to 10 g, of active ingredient.

The production of the above mentioned pharmaceutical compositions and medicaments is carried out by any method known in the art, for example, by mixing the active ingredients with the diluent(s) to form a pharmaceutical composition (e.g. a granulate) and then forming the composition into the medicament (e.g. tablets).

This invention further provides a method of combating (including prevention, relief and cure of) the above mentioned diseases in human and non-human animals, which comprises administering to the animals compounds of the invention alone or in admixture with a diluent or in the form of a medicament according to the invention.

It is envisaged that these active compounds will be administered perorally, parenterally (for example intramuscularly, intraperitoneally, subcutaneously or intravenously), rectally or locally, preferably orally or parenterally. Preferred pharmaceutical compositions and medicaments and therefore those adapted for oral or parenteral administration, such as tablets, pills, dragees or capsules, or injection solutions or suspensions or ampoules thereof, respectively. Administration in the method of the invention is preferably orally or parenterally.

In general it has proved advantageous to administer amounts of from 5 to 1000 mg, preferably from 20 mg to 200 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, while in other cases the upper limit mentioned must be exceeded to achieve the desired results. Where larger amounts are administered it can be advisable to divide these into several individual administrations over the course of the day. An individual administration preferably contains from 1 to 250, most preferably from 10 to 100, mg/kg of body weight.

The particular optimum dosage required and the type of administration of the active compounds can easily be determined by anyone skilled in the art, on the basis of his expert knowledge. In the case of intravenous application, one ampule contains, for example, 2 g of D-α-[(3-methylsulphonyl-imidazolidin-2-on-1-yl)-carbonylamino]-benzylpenicillin and 1 g of 3-phenyl-5-methyl-4-isoxazolylpenicillin.

When used as feedstuff additives, the new synergistic active compound mixtures can be administered in the customary concentrations and formulations together with the feedstuff or with feedstuff formulations or with the drinking water. By this means it is possible to prevent, alleviate and/or cure an infection by Gram-negative or Gram-positive bacteria and also to achieve promotion of growth and better utilization of the feedstuff.

The new synergistic active compound mixtures are distinguished by powerful antibacterial actions, which have been tested in vivo and in vitro, and by oral resorbability.

The activity of the active compound combinations according to the invention may be illustrated by the following table:

| Minimum inhibitory concentration in mcg/ml: | | | | | | |
| --- | --- | --- | --- | --- | --- | --- |
| | Substances: | | | | | |
| Germ: | 1 | 2 | 3 | 4 | 5 | 1 + 3 |
| Proteus morg. 1102 | >512 | >512 | >512 | >512 | >256 | 32 + 32 |
| Proteus mirabilis v 468 | >512 | >512 | 512 | 512 | >256 | 256 + 256 |
| Proteus rettgeri 985 | 128 | >512 | >512 | 512 | >256 | 64 + 64 |
| E. coli v 250 | 128 | 256 | 512 | 512 | >256 | 32 + 32 |
| E. coli v 1465 | 256 | >512 | >512 | 512 | >256 | 128 + 128 |
| Proteus morganii v 1306 | 2 | 32 | 512 | >512 | 512 | — |
| Proteus morganii 1272 | 16 | 128 | >512 | >512 | >256 | 16 + 16 |
| Klebsiella v 1673 | 64 | 256 | 256 | 512 | 512 | 32 + 32 |

| | Substances: | | | | |
| --- | --- | --- | --- | --- | --- |
| Germ: | 1 + 4 | 2 + 3 | 2 + 4 | 5 + 3 | 5 + 4 |
| Proteus morg. 1102 | 32 + 32 | — | — | >256 | >256 |
| Proteus mirabilis v 468 | 128 + 128 | >256 + 256 | >256 + 256 | >256 + 256 | >256 + 256 |
| Proteus rettgeri 985 | 64 + 64 | 256 + 256 | 256 + 256 | >256 + 256 | 256 + 256 |
| E. coli v 250 | 32 + 32 | 128 + 128 | 128 + 128 | >256 + 256 | 256 + 256 |
| E. coli v 1465 | 128 + 128 | >256 + 256 | >256 + 256 | >256 + 256 | >256 + 256 |
| Proteus morganii v 1306 | 1 + 1 | 16 + 16 | 1 + 1 | 64 + 64 | 32 + 32 |
| Proteus morganii 1272 | 8 + 8 | 64 + 64 | 0.5 + 0.5 | 64 + 64 | 32 + 32 |

| | Minimum inhibitory concentration in mcg/ml: | | | |
|---|---|---|---|---|
| Klebsiella v 1673 | 32 + 32 | 128 | 256 | 256 |

Explanation:
Substance 1 = D-α-[(3-methylsulphonyl-imidazolidin-2-on-1-yl)-carbonylamino]-benzylpenicillin.
Substance 2 = D-α-[(imidazolidin-2-on-1-yl)-carbonylamino]-benzylpenicillin.
Substance 3 = 3-phenyl-5-methyl-4-isoxazolylpenicillin.
Substance 4 = 3-(2,6-dichlorophenyl)-5-methyl-4-isoxazolylpenicillin.
Substance 5 = α-amino-benzylpenicillin The minimum inhibitory values (MIC) in the table were determined in a Muller-Hinto nutrient broth in a series dilution test using an inoculation of $2 \cdot 10^5$ bacteria per ml, after incubation for 24 hours. In testing the active compound mixture, the weight ratio of substance 1, 2 or 5 to substance 3 or 4 was 1:1 in each small test-tube. If the amounts by weight are converted into units (IU), this gives, for example, 1,700 IU for 1 mg of substance 5 (rounded off) and 1,100 IU/ml for substance 1.

The difference in favor of substance 1 is thus increased by a factor of 1.5, compared with substance 5.

It will be appreciated that the instant specification and examples are set forth by way of illustration and not limitation, and that various modifications and changes may be made without departing from the spirit and scope of the present invention.

What we claim is:

1. A pharmaceutical composition containing an antibacterially effective amount of (A) D-α-[(imidazolidin-2-on-1-yl)-carbonylamino]-benzylpenicillin, D-α-[(3-methylsulphonyl-imidazolidin-2-on-1-yl)-carbonylamino]-benzylpenicillin, or a pharmaceutically acceptable salt thereof, and an approximately equal amount by weight of (B) 3-(2,6-dichlorophenyl)-5-methyl-4-isoxazolylpenicillin, 3-phenyl-5-methyl-4-isoxazolylpenicillin, or a pharmaceutically acceptable salt thereof.

2. A composition according to claim 1, in which (A) is D-α-[(3-methylsulphonyl-imidazolidin-2-on-1-yl)-carbonylamino]-benzylpenicillin and (B) is 3-phenyl-5-methyl-4-isoxazolylpenicillin, or a pharmaceutically acceptable salt thereof.

3. The composition according to claim 1, in which the active compounds are in the form of sodium salts.

4. An animal feedstuff comprising feed and a composition according to claim 1.

5. A method of combating disease caused by bacteria and bacteria-like micro-organisms in human and non-human animals which comprises administering to the animals an antibacterially effective amount of a composition according to claim 1.

6. A method according to claim 5, in which the active ingredients are administered in an amount of about 5 to 1000 mg of total active ingredients per kg body weight per day.

7. A method according to claim 5, in which the animals are ruminants.

* * * * *